United States Patent [19]

Bach et al.

[11] Patent Number: 4,680,276

[45] Date of Patent: Jul. 14, 1987

[54] METAL POLYPEPTIDES

[75] Inventors: Jean-Francois Bach; Mireille Dardenne, both of Paris; Jean-Marie Pleau, Palaiseau; Jean Hamburger; Evangheios Bricas, both of Paris; Jean Martinez, General Leclerc; Didier Blanot, Bures S. Yvette; Genevieve Auger, Limours; Pierre Lefrancier, Bures sur Yvette; Bernard Amor, Paris, all of France

[73] Assignee: Institut National de la Sante et de la Recherche Medicale, Paris, France

[21] Appl. No.: 648,834

[22] Filed: Sep. 10, 1984

Related U.S. Application Data

[63] Continuation-in-part of Ser. No. 265,996, May 21, 1981, and Ser. No. 541,475, Oct. 13, 1983, abandoned, which is a continuation of Ser. No. 320,880, Nov. 13, 1981, abandoned, which is a continuation of Ser. No. 909,163, May 24, 1978, Pat. No. 4,301,065.

[30] Foreign Application Priority Data

May 22, 1980 [GB] United Kingdom ............... 8017029
Sep. 22, 1980 [GB] United Kingdom ............... 8030507
Sep. 9, 1983 [JP] Japan ............................. 58-166414

[51] Int. Cl.$^4$ ..................................... G01N 33/536
[52] U.S. Cl. ........................................ 436/542; 514/2; 514/6; 530/328; 530/329; 530/330; 530/345; 436/804; 436/817

[58] Field of Search ............... 436/542, 804, 817; 530/328, 329, 330, 345; 514/2, 6

[56] References Cited

U.S. PATENT DOCUMENTS

| | | | |
|---|---|---|---|
| 4,010,148 | 3/1977 | Goldstein | 424/172 |
| 4,046,877 | 9/1977 | White et al. | 424/177 |
| 4,079,127 | 3/1978 | Goldstein et al. | 424/177 |
| 4,116,951 | 9/1978 | Wang | 424/177 |
| 4,128,637 | 12/1978 | Naylor et al. | 424/177 |
| 4,129,648 | 12/1978 | Collier et al. | 424/177 |
| 4,148,788 | 4/1979 | Wang | 424/177 |
| 4,239,498 | 12/1980 | Rule | 424/177 |
| 4,293,455 | 10/1981 | Merrifield et al. | 424/177 |
| 4,297,276 | 10/1981 | Goldstein et al. | 424/177 |
| 4,301,065 | 11/1981 | Bach et al. | 260/112.5 R |

OTHER PUBLICATIONS

Low et al, J. Biol. Chem, 254(1979), 981–986.
Goldstein et al., Proc. Natl. Acad. Sci. USA, 74(1977), 725–729.

*Primary Examiner*—Christine M. Nucker
*Attorney, Agent, or Firm*—Weiser & Stapler

[57] ABSTRACT

The present invention relates to novel peptide compounds, of which the chemical structure is related to that of the polypeptide hormone having a thymic activity, isolated from the blood serum of pig, and the application of these novel compounds for therapeutic purposes. This invention also relates to intermediates useful in preparing the active compounds of the invention.

47 Claims, 6 Drawing Figures

FIG_1

FIG.2

FIG_3

FIG_4

FIG_5

METAL POLYPEPTIDES

This application is a continuation in part of application Ser. No. 265,996 filed May 21, 1981, and application Ser. No. 541,475 filed Oct. 13, 1983, now abandoned, which is a continuation of application Ser. No. 320,880 filed Nov. 13, 1981, now abandoned, which is a continuation of application Ser. No. 909,163 filed May 24, 1978, now Pat. No. 4,301,065.

The present invention relates to novel peptide compounds, of which the chemical structure is related to that of the polypeptide hormone having a thymic activity, isolated from the blood serum of pig, and the application of these novel compounds for therapeutic purposes. This invention also relates to intermediates useful in preparing the active compounds of the invention.

It has been well established that the T Lymphocytes acquire their immunocompetence under the influence of the thymus. This differentiating action of the thymus has formed the subject of numerous research procedures since the discovery of the immuno-suppressive effects of neonatal thymectomy. Experiments which show the respiration of the immunitary competence of mice thymectomised at birth by thymus grafts placed in diffusion chambers impermeable to the cells or by a-cellular thymic extracts have suggested that the thymus plays the part of an endocrine gland and prepares a hormone which is introduced into the blood circulation.

The isolation and the characterisation of a hormone, which is referred to as "seric thymic factor" (FTS), present in the serum of several species of mammals, particularly pigs, have formed the subject of recent publications.

The invention also relates to radioactive tracers obtained from these new products and to the use of these tracers in a process for the radio-immunological detection of FTS in a sample.

The thymic origin of FTS, suggested by the disappearance of FTS from the serum after thymectomy, was recently directly demonstrated by the localisation by immunofluorescence in the thymic epithelium of purified antibodies produced against synthetic FTS.

FTS has numerous in vitro and in vivo biological activities, including in particular the induction of the theta antigen characteristic of the T lymphocytes in mice in theta-negative cells of bone marrow and spleen from thymectomised mice which form rosettes.

FTS has been characterised by a biological test, commonly known as the "rosette test", which is based on induction of the sensitivity to azathioprine of rosette-forming cells from the spleen of thymectomised mice. The rosette test was described by J. F. Bach and M. Dardenne in Immunology, 25, 353 (1973).

This test is based on the ability of FTS to render theta-positive and azathioprine-sensitive the theta-negative rosette-forming cells obtained from the spleen of adult thymectomised mice. Azathioprine is a purine analog which, like anti-theta serum, inhibits the formation of thymus-dependent rosette-forming cells. In normal mice, rosette formation is inhibited by 1 ug/ml of azathioprine whereas, in adult thymectomised mice, from 50 to 100 ug/ml of this compound are necessary to inhibit rosette formation. FTS as well as the thymic extracts imparts to the rosette-forming cells of adult thymectomised mice, after incubation for 90 minutes at 37° C., a sensitivity to azathioprine identical with that of the rosette-forming cells of normal mice, which may be used as a basis for a reproducible and quantitative in vitro and in vivo biological test.

In the rosette test, the thymic activity of a sample (FTS or thymic extract or a serum sample) is determined by incubation in a haemolysis tube with $3 \times 10^6$ cells from the spleen of adult C 57/B1 6 mice (supplied by the Centre d'Elevage des Animaux de Laboratoire du C.N.R.S. 45 Orleans, La Source) which had been thymectomised ten to twenty days previously. The thymectomy method is described by M. Dardenne and J. F. Bach in Immunology 25, 343 (1973) on page 344, the contents of this article being incorporated here for reference purposes.

Incubation is carried out for 90 minutes at 37° C. in the presence of azathioprine (Az) in a concentration of 10 ug/ml.

This concentration is intermediate between the minimal Az concentration which inhibits 50% of the rosette-forming cells (RFC) from the spleen of normal mice (1 ug/ml) and that which inhibits the rosette-forming cells of thymectomised animals (50 ug/ml). After incubation, $12 \times 10^6$ sheep red blood cells (SRBC) are added to the tubes containing the cells and the sample. The cells and the sample are centrifuged for six minutes at 1400 revolutions per minute and are resuspended gently and carefully by rotation on a rotary agitator (10 cm in diameter) at low speed (10 revolutions per minute). The RFC are counted in a haematocytometer. In the absence of thymic activity, the number of RFC is $1210/10^6$ cells $\pm 120$ (standard deviation, SD). In the presence of thymic activity, the quantity of RFC is reduced to a level of 200 to $400/10^6$ cells. In the absence of Az, the FTS does not inhibit the RFC.

In vitro rosette test:

The thymic activity is defined as the lowest concentration of the sample which induces inhibition of more than 50% of the rosette-forming cells from the spleen of adult thymectomised mice in the presence of 10 ug/ml of azathioprine.

In vivo:

(a) The activity of the serum is expressed as the thymic factor level (determined by the rosette test described above) in the serum of adult thymectomised mice collected two or four hours after the injection of 0.1 ng or 1 ng of sample absorbed on carboxymethyl cellulose or injected alone: the activity of the serum is expressed as the highest dilution of the serum allowing the inhibitition of 50% of the rosette-forming cells.

(b) The activity of the spleen cells is expressed as the sensitivity to azathioprine of these cells of adult thymectomised mice isolated 24 hours after the injection of 0.1 ng to 1 ng of sample absorbed on carboxymethyl cellulose or injected alone.

It has thus been shown that the seric thymic factor is a nonapeptide, which is characterised by the sequence of the following amino acids:

Pyro-Glu-Ala-Lys-Ser-Glu-Gly-Gly-Ser-Asn        (I)

Now the chemical synthesis of the seric thymic factor having the structure (I) as indicated above has just been carried out, as well as that of a family of peptide compounds of related structure, including therein that of another form or the seric thymic factor, corresponding to the following sequence:

X-Gln-Gly-Gly-Ser-Asn in which X represents Ser, Lys-Ser-, Ala-Lys-Ser-, Glx-Ala-Lys-Ser-; and when X represents Glx-Ala-Lys-Ser-, Y may in addition represent -Ser; as well as their derivatives which comprise 1 or 2 modified amino acids, wherein Glx represents PyroGlu or Gln, their derivatives comprising 1 or 2 modified amino acides, and the hexapeptides, heptapeptides and octapeptides of these compounds, which preserve their C-terminal or N-terminal sequence; which are biologically active when bonded to a metal that is capable of forming a complex of coordination number IV having a tetrahedral configuration, in particular a metal which is divalent or trivalent.

The metal may also be in the form of a metalloprotein wherein the metal forms a bond between the peptide and a protein, and possess the desired activity.

The metal which is involved may be a divalent metal, such as manganese, iron, nickel, zinc, or copper, or a trivalent metal such as aluminum, gallium, chromium and nickel, but zinc is the preferred metal.

The quantity of metal which is in the complexes of the invention, as determined by atomic spectrometry, must be such that the weight ratio of metal to the complex is greater than 1/200, preferably 1:1.

The polypeptides which can be utilized to prepare the active compounds which are bonded to the metal in accordance with the invention are those which are disclosed in U.S. Pat. No. 4,301,065, which is incorporated herein in its entirety by reference. Among those disclosed are the polypeptides having the sequence X-Gln-Gly-Gly-Y wherein Y is -Ser-Asn and X is Lys-Ser, Ala-Lys-Ser or Glx-Ala-Lys-Ser- wherein Glx is PyroGlu or Gln; and when X is Glx-Ala-Lys-Ser., Y can also be -Ser; and said polypeptide in which one or two amino acids in said sequence are replaced as follows:

1. $Ser^4$ or $Ser^8$ is replaced by: Thr, Ala or N-methyl-Ser;
2. PyroGlu is replaced by Pro;
3. $Lys^3$ is replaced by: ($N^6$-acetyl)-Lys, 2-aminohexanoyl, 2-6-diaminohexynoyl, Arg, Har or Orn;
4. $Gln^5$ is replaced by: Glu, Met(O), Asn or Nor-Val;
5. $Gly^6$ or $Gly^7$ either one individually, is replaced by: Ala, Sar or Leu, and
6. $Asn^9$ is replaced by: Asp, Gln, -Ala-NH, and Asn-NH$_2$, and the polypeptides, PyroGlu-Ala-Lys-Ser-Gln-Gly-Gly-Gly-Ser-Asn, and PyroGlu-Ala-Lys-Ser-Gln-Gly-Ser-Asn.

More particular, some of the polypeptides which are useful as intermediates for preparing the active metal containing compounds are:
PyroGlu-D-Ala-Lys-Ser-Gln-Gly-Gly-Ser-Asn
D-Ala-Lys-Ser-Gln-Gly-Gly-Ser-Asn
PyroGlu-Ala-Lys-Ala-Gln-Gly-Gly-Ser-Asn
PyroGlu-Ala-Orn-Ser-Gln-Gly-Gly-Ser-Asn
PyroGlu-Ala-Lys-Ser-Glu-Gly-Gly-Ser-Asn
Orn-Ser-Gln-Gly-Gly-Ser-Asn
PyroGlu-Ala-Hep-Ser-Gln-Gly-Gly-Ser-Asn
PyroGlu-Ala-Lys-Ser-Gln-Gly-Gly-Ser-Asn-NH$_2$
PyroGlu-Ala-Lys-Ser-Asn-Gly-Gly-Ser-Asn
PyroGlu-Ala-Lys-Ser-Nva-Gly-Gly-Ser-Asn
Z-Ala-Lys-Ser-Gln-Gly-Ser-Asn
D-PyroGlu-Ala-Lys-Ser-Gln-Gly-Gly-Ser-Asn
D-Gln-Ala-Lys-Ser-Gln-Gly-Gly-Ser-Asn
Pro-Ala-Lys-Ser-Gln-Gly-Gly-Ser-Asn
PyroGlu-Ala-Har-Ser-Gln-Gly-Gly-Ser-Asn In accordance with one feature of the invention the invention, there is provided novel compositions and method for the treatment of rheumatoid polyarthritis.

Rheumatoid arthritis (RA) or chronic evolutive polyarthritis (CEP) is, as its name indicates, a chronic disease characterized by inflammatory articular symptoms which preferentially affect distal articulation of the limbs.

This disease causes pain, swelling of joints, stiffness and deformation of the limbs, accompanied by a considerable decrease in the gripping strength and by the holding of incorrect postures, leading to more or less complete functional infirmity.

The treatment of this disease prior to the present invention involved the use of slow-acting antirheumatic agents, corticoids, various antiphlogistic agents and antalgics.

It has now been found that serum thymic factor (STF) bonded to metal that is capable of forming a complex having a tetrahedral configuration, particularly, a zinc atom, and its derivatives, have a useful action in the treatment of this disease.

As has been indicated above, it has now been discovered that when FTS and its derivatives are bonded to a metal atom, in particular bonded to a zinc atom, they are useful in the treatment of rheumatoid polyarthritis, significantly improving, in particular, the Ritchie index and various inflammatory symptoms. This includes where the metal is additionally bonded to a protein substance.

Furthermore, according to the invention, the product as described herein, for example, when the metal is zinc, injected in a dose of 0.1 ng per mouse, has an in vivo activity in the rosette test which is ten times greater than that obtained for the reference FTS injected in a dose of 1 ng per mouse.

The invention also relates to a process for the preparation of new products prepared from FTS or its analogs or derivatives, which comprises treating FTS or one of its analogs or derivatives with a metal or a metal-containing protein.

In a preferred embodiment of the invention, the FTS or one of its analogs or derivatives is brought into contact with the metal or one of its salts at a pH of between 7 and 9 for ten to thirty minutes at ambient temperature, for example, from 20° to 37° C.

In this embodiment, it is of advantage to use a proportion of 1 mole of FTS or an analog or derivative of FTS for 0.1 to 10 moles of the metal or of one of its salts, preferably 1 mole of the metal or of one of its salts.

In another embodiment of the process according to the invention, the new products are prepared by treating FTS or one of its analogs or derivatives with a metal-containing protein substance.

This metal-containing protein substance may be, for example, a serum fraction or a fraction of a thymic extract. The metal containing protein substance may be a metalloprotein or metalloenzyme. For example, the metal-containing protein substance used may be a fraction of the Thymosine Fraction 5, which will be referred hereinafter as the "activating fraction" by virtue of its activating properties with respect to FTS or its analogs and derivatives.

In 1965, A. L. Goldstein et al isolated from calf thymus a more or less impure preparation which they called Thymosine Fraction 5 and which is a mixture of numerous polypeptides having various biological activities.

This preparation has been used in humans in phase 1 and 2 clinical trials with as yet inconclusive, but promising results.

More recently, A. L. Goldstein published the sequence of certain peptides contained in the Fraction 5, namely the thymosines $\mathbf{1}'\mathbf{1}'.\ldots$, but none of these peptides has been found to show any structural similarity to FTS.

Our own preliminary studies have shown that the Thymosine Fraction 5 contained one or more substances which are active in the above-mentioned rosette test and having physical or chemical properties comparable with those of FTS (molecular weight, electrical charge, aminoacid composition).

The above-mentioned activating fraction is prepared by fractionating Thymosine Fraction 5 in a column of G-100 (Pharmacia 0.9 cm × 100 cm) in a pH 7.3 0.2 M phosphate buffer to eliminate the molecular(s) similar to FTS, only the eluted fraction with elution volumes of from 15 to 22 ml being retained.

This fraction contains molecules having a molecular weight in the range from 7500 to 12500 (tracers used: IGG, bovine albumin, Cytochrome C and tritiated FTS).

This fraction is sensitive to heat: its activity is destroyed by heating to 60° C. in less than 15 minutes and to 100° C. in less than 5 minutes.

This fraction, which itself has no activity in the rosette test shows activating properties with respect to FTS or its analogs and derivatives insofar as it enables their biological activity to be increased by a factor of approximately $10^3$.

The process for preparing the new products from the activating fraction emanating from the Thymosine Fraction 5 is characterised in that FTS or one of its analogs or derivatives in incubated with this activating fraction, the mixture obtained after incubation is fractionated and the fraction showing the greatest activity in the rosette test is selected.

In this process, the incubation temperature is in the range from 30° to 40° C., the incubation time is between 10 minutes and 1 hour and incubation is carried out at a pH value in the range from 6 to 8.

The particularly preferred conditions comprise carrying out incubation for 20 minutes at a temperature of approximately 37° C. and at a pH value of 7.3.

Irrespective of the process used (treatment with a metal or metal salt or treatment with a metal-containing protein substance), it is preferable to eliminate at the outset any trace of metal which may be present in the preparation of FTS or one of its analogs or derivatives by means of a chelating agent capable of chelating metals, for example by chromatography in a column of chelating resin of the "Chelex 100" type. This allows a chemically homogeneous product to be obtained which, after being treated with the metal in an environment where it could form a salt or with one of its salts, produces a homogeneous product with reproducible results, these products thus being acceptable for pharmaceutical application. The preferred salts are metal chloride, acetate or sulfate.

The FTS or the FTS analogs or derivatives which are used in the process according to the invention are those which have been synthesized in the liquid phase by the method described by Bricas, E., Martinez J., Blanot, D., Auger, G., Dardenne, M., Pleau, J. M., and Bach, J. F., 5th Intern. Peptide Symposium, La Jolla, Calif., U.S.A., June 1977, and those described in French Patent Application No. 77 15963 filed May 25, 1977 and in its Addition No. 78 11870 filed Apr. 21, 1978.

The Thymosine Fraction 5 used for preparing the activating fraction according to the invention was obtained by A. L. Goldstein's method (Goldstein A. L., Salter, F. D. and White, A., 1966, Proc. Nat. Acad. Sci. USA, 56, 1010–1017, and Goldstein, A. L., Guha, A., Zatz, M. M., Hardy, M., White, A., Proc. Nat. Acad. Sci. USA, 69, 1800–1803).

Other features of the invention will now be described in the following Examples.

EXAMPLE 1

Preparation of the activating fraction:

The Thymosine Fraction 5 prepared by the above-mentioned method was fractionated in a first stage in a column of G-100 (Pharmacia 0.9 cm × 100 cm) in a 0.2 M pH 7.3 phosphate buffer to eliminate the above-mentioned molecule(s) similar to or identical with FTS.

Only the eluted fractions with elution volumes of from 15 to 22 ml are retained and used for the described tests. These fractions, which will be referred to hereinafter as "activating fractions", contain molecules having molecular weights in the range from 7500 to 12,500 and do not show any activity in the rosette test.

The quantities of activating fractions used will be expressed in the following equivalents of Fraction 5 (EqF 5), i.e. in equivalents of the quantity of Fraction 5 used for its preparation.

EXAMPLE 2

Preparation of an activated product:

1 mg of FTS corresponding to the formula p Glu-Ala-Lys-Ser-Gln-Gly-Gly-Ser-Asn synthesized in the liquid phase by the method described above is incubated with 50 mg (EqF 5) of the activating fraction of Example 1 in a tube of plastics material for 20 minutes at 37° C. in a 0.2 M pH 7.3 phosphate buffer.

After incubation, the mixture is applied to a column of Sephadex G-25 and the active fraction detected by the rosette test is recovered in the fractions having an elution volume of from 1.8 to 2.2 Vo.

This fraction is freed from salts by dry filtration on an Amicon UM 2 membrane and is then taken up in 0.02 M pH 6.1 phosphate buffer and applied to a column of carboxy methyl cellulose (Whatman) balanced by the same phosphate buffer.

An NaCl gradient is applied after a passage of 50 ml of the initial buffer. The fractions showing activity in the rosette test are recovered in the fractions containing 0.12 M of NaCl.

The fractions obtained after incubation with the activating fraction are from $10^2$ to $10^3$ times more active than the initial preparation of FTS.

These active fractions are then freed from salts by dry filtration on an Amicon UM 2 membrane and subsequently subjected to an aminoacid analysis.

The results of this analysis show that the fraction thus recovered has a high biological activity and an aminoacid composition compatible with that of the initial FTS.

Incubation of the FTS with the activating fraction according to the invention emanating from a thymic extract increased the biological activity of the synthetic FTS by a factor of $10^3$.

The aminoacid analysis and the behaviour on Sephadex G-25 and carboxymethyl cellulose of the "activated" preparation confirm that the FTS is the synthetic FTS itself in activated form.

In the presence of the activating fraction (as distinct from the FTS), the FTS is transformed after 20 minutes at 37° C. and this transformation increases its biological activity very significantly.

As in the case of treatment with a metal or metal salt, this transformation is indicative of the fixing of a metal to the starting product.

EXAMPLE 3

Activation by a Metal

I. Materials and Methods

A. Reactants:

The synthetic FTS was prepared by the method described above. The tritium-labelled FTS was obtained by the tritiation of a FTS analog containing a lysine having an acetylenic bond (Sasaki A. W., Morgat J. L. and E. Bricas, 16th European Symposium on Peptides, Elsinger, Denmark, Sept., 1980, K. Brungeldt, page 224).

The zinc was used in the form of its optionally radial-labelled chloride ($^{65}Zn\ Cl_2$).

B. Chromatography:

The treatment with Chelex 100 (Biorad Lab.) was carried out by mixing 0.2 ml of the solution containing the product under investigation with 0.2 ml of a 50 mg/ml suspension of Chelex. Chromatography on Biogel P-2 was carried out using plastic columns (60×0.9 cm).

C. Rosette test:

The spleen cells of C56BL/6 mice thymectomised at the age of 6 weeks are resistant to azathioprine (10 ug/ml). The thymic extracts or the FTS or the serums containing it provide the cells with their sensitivity to azathioprine. The test results are expressed by the minimum inhibiting concentration of FTS or the maximum inhibiting dilution of serum.

II. RESULTS

A. Loss of biological activity of FTS in the presence of a metal-chelating agent An aqueous solution of synthetic FTS is contacted with Chelex 100 resin. The FTS which is not retained by the resin is tested in the rosette test. Table I below shows that the FTS has lost most of its in vitro and in vivo activity after this treatment. Similar results are observed with natural FTS (normal serum ultrafiltrate of mice) treated under the same conditions.

B. Biological activity of FTS pretreated by passage over Chelex 100 after the addition of zinc or other metals The addition of 10 ng of $ZnCl_2$ to 100 ng of FTS (synthetic or natural) pretreated by passage over Chelex 100 followed by incubation for 10 minutes at 20° C. brings about 1 significant increase in the in vivo and in vitro biological activity. Metals other than zinc are capable of activating FTS: aluminum (as active as zinc), copper manganese, chromium, gallium, iron and nickel, whereas indium, thallium, cadmium, lead, cobalt and tin have no effect.

C. Direct demonstration of the fixing of zinc to the FTS molecule

The tritiated FTS is eluted with distilled water from a column of Biogel P-2 in a single peak (fractions 10–14, $V_eV_o$: 1.3) which recovers the biological activity of which the level is higher than in the very first fractions (10–12). Applied to the same column, the $^{65}ZnCl_2$ is eluted with a $V_e/V_o$ of 2.2 (fractions 19–22). When a mixture of 0.1 μg of tritiated FTS (previously passed over Chelex 100) and 10 to 30 ng of $^{65}ZnCl_2$ is applied to the column of Biogel P-2, the radioactivity corresponding to $^{65}Zn$ appears in two peaks: the first, which is the larger of the two, corresponds very precisely to the biological activity and to the first half of the radioactivity peak of the tritiated FTS (fractions 9 to 12), whilst the second corresponds to that of the free zinc (fractions 19 to 23). This result shows that a percentage of the order of 1% of zinc is fixed to the FTS.

III. DISCUSSION

These tests show that the FTS loses some of its activity after passage over a metal-chelating resin and recovers its activity completely after the addition of various metal salts, such as those of zinc or aluminum, and partly after the addition of certain others. The zinc is fixed to the FTS with an affinity constant sufficient to allow separation from the free zinc on Biogel P-2. Thus, the FTS becomes increasingly activated after certain metals, particularly zinc, have been arrested.

The presence of biological activity and the fixing of zinc in the very first fractions of the FTS peak eluted on Biogel P-2 indicates the existence of two forms of FTS. Only the first of these two forms to which the zinc is fixed is biologically active in the rosette test. Other results indicate that these two forms also differ in their antigenicity.

Table 1 below shows the results of the in vivo and in vitro tests and demonstrates the increase in the biological activity of the activated products according to the invention obtained by treating FTS either with salt or with the activating fraction emanating from the Thymosine fraction 5.

TABLE I

| | In vitro activity: minimum inhibiting concentration | In vivo activity: inhibiting dilution of the serum 30 minutes after the administration of 1 ng of FTS |
|---|---|---|
| Synthetic FTS | $5.10^{-6}$ ng/ml | 1/80 000 |
| Synthetic FTS passed over Chelex 100 | 1 ng/ml | 1/256 |
| Synthetic FTS passed over Chelex 100 + zinc chloride | $2.10^{-7}$ ng/ml | $1/10^6$ |
| Zinc chloride alone | no activity | 1/4 |
| Synthetic FTS | $5.10^{-6}$ ng/ml | 1/80 000 |
| Synthetic FTS passed over Chelex 100 + activating fraction | $3.10^{-9}$ ng/ml | $1/10^6$ |
| Synthetic FTS passed over Chelex 100 + activating fraction passed over Chelex 100 | 1 ng/ml | 1/100 |
| Normal mouse serum (ultrafiltrate) | | 1/128 |
| Normal serum passed over Chelex 100 | | 1/4 |
| Normal serum passed over Chelex 100 + zinc chloride | | 1/128 |
| Normal serum passed over Chelex 100 + activating fraction | | 1/128 |
| Normal serum passed over Chelex 100 + activating fraction passed over Chelex 100 | | 1/4 |
| Serum from thymectomised Mice | | 1/4 |
| Serum from | | 1/4 |

TABLE I-continued

| | In vitro activity: minimum inhibiting concentration | In vivo activity: inhibiting dilution of the serum 30 minutes after the administration of 1 ng of FTS |
|---|---|---|
| thymectomised mice + zinc chloride | | |
| Serum from thymectomised mice + activating fraction | | 1/4 |

Table I shows that the FTS pretreated by passage over Chelex 100 subsequently returns to a substantially increased in vitro biological activity level and to an even higher in vivo biological activity level after treatment with a metal or with the activating fraction, this metal and this activating fraction themselves showing no biological activity in the rosette test.

Table I also shows that certain products according to the invention are active in concentrations below $10^{-9}$ ng/ml.

For the in vivo tests, the activated derivatives of the invention were injected into thymectomised mice which were six weeks old and used eight weeks after thymectomy. After 30 minutes in the serum they induce the appearance of a biological activity which is from 10 to 100 times greater than that obtained using natural FTS, imparting to the rosette-forming spleen cells a sensitivity to azathioprine.

Figure 1:
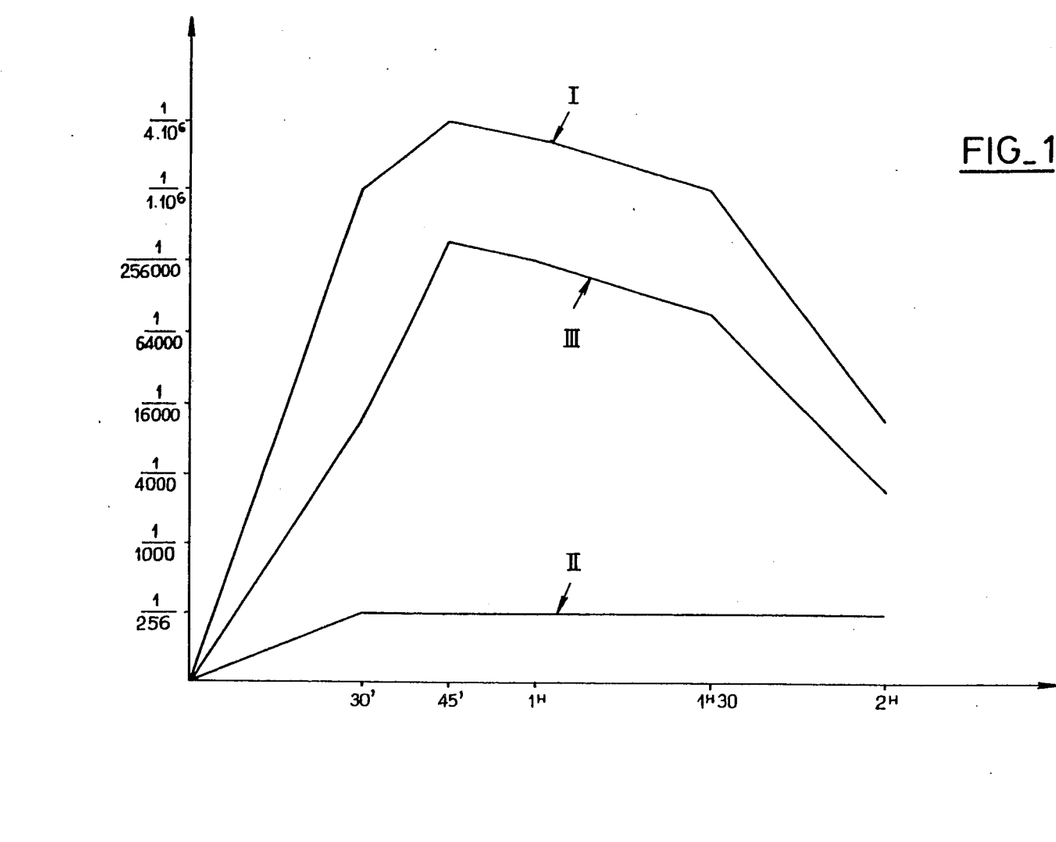

This increase in biological activity is clearly shown in FIG. 1 which compares the biological activity of the FTS, passed over a chelating resin, then treated with zinc sulfate at pH 7 and injected in a dose of 0.1 ng per mouse (curve I) with the activity of the FTS which has merely been passed over the resin, then injected in a dose of 1 ng per mouse (curve II), and with the activity of the reference FTS which was injected in a dose of 1 ng per mouse (curve III).

The curves of FIG. 1, as well as those of FIGS. 2 to 6, express the variation in the activity of the product injected in the serum, expressed by the active serum dilution as a function of the time elapsed after the injection. The curves of FIG. 1 compare the activity of the reference FTS, injected in the mouse, the activity of the FTS treated with a chelating resin and injected into the mouse, and the activity of a product according to the invention which was injected in the mouse, the latter being much more active.

Figure 2:
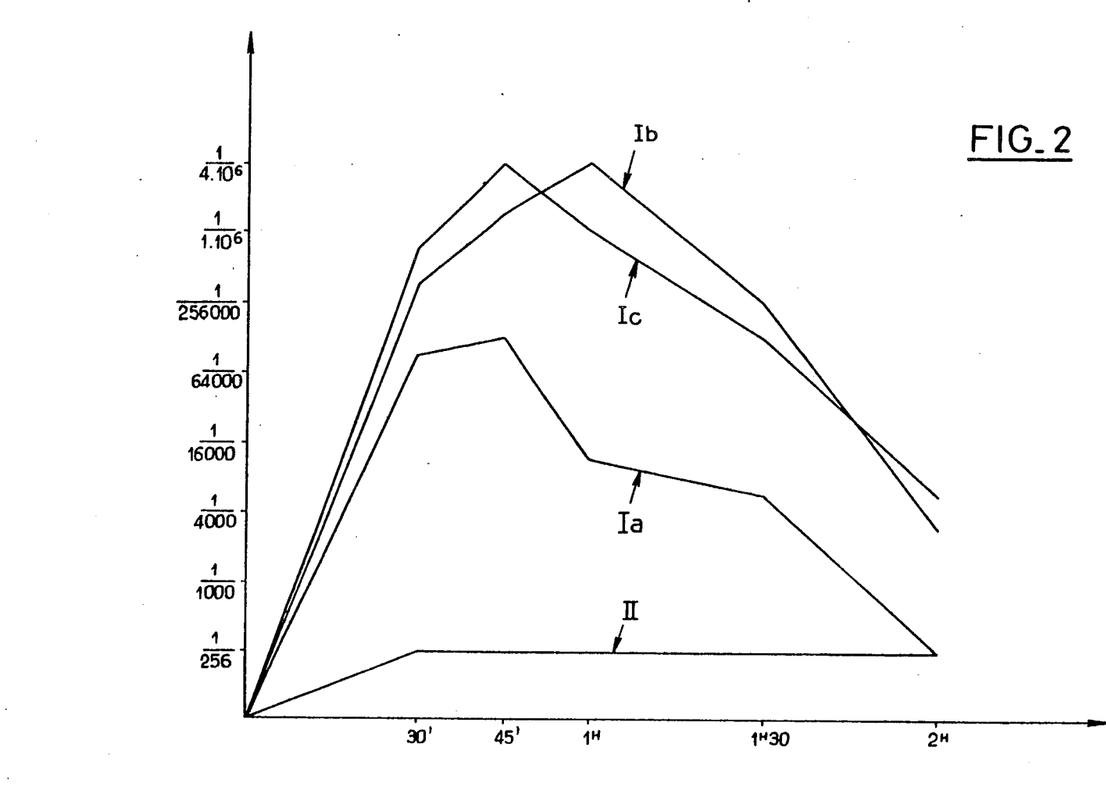

FIG. 2 shows the activation which was obtained in vivo by FTS passed over a chelating resin, then treated with zinc sulfate using various weight ratios of Zn/FTS 0.01(curve Ia); 0.1 (curve Ib) and 1 (curve Ic)) and injected into the mouse, in comparison with the FTS which was merely passed over a chelating resin and injected into the mouse (curve II).

The best activation is obtained for weight ratios of from 0.1 to 10.

Figure 3:
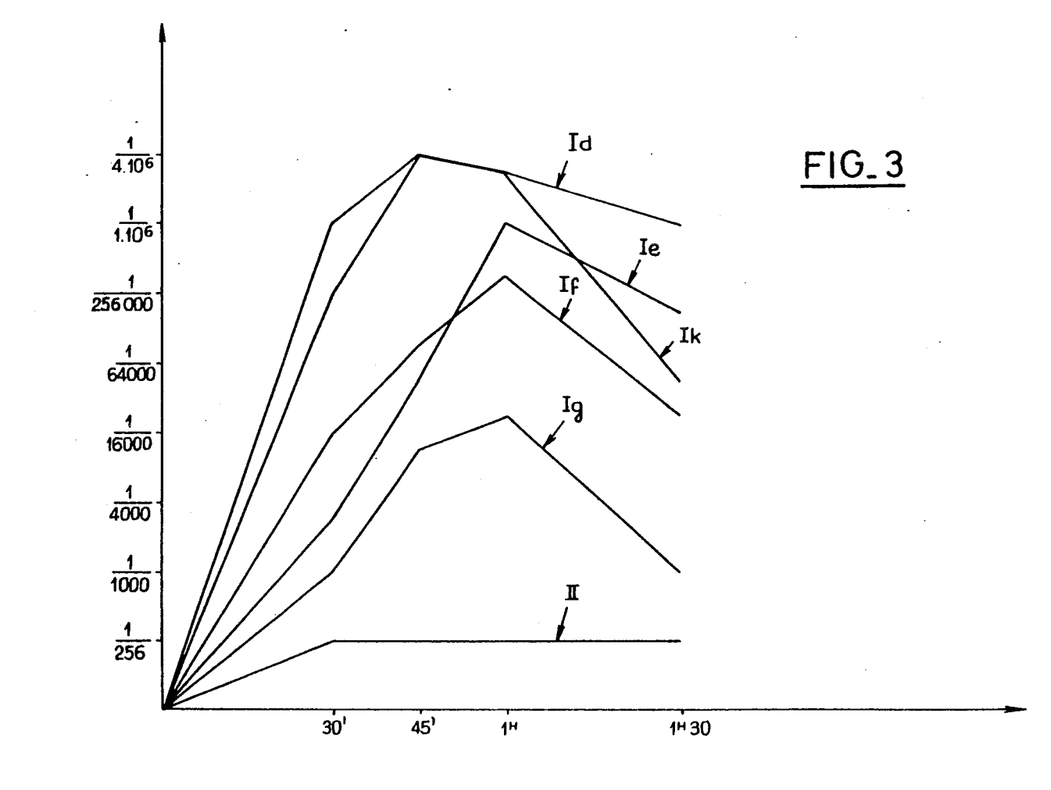
Figure 4:
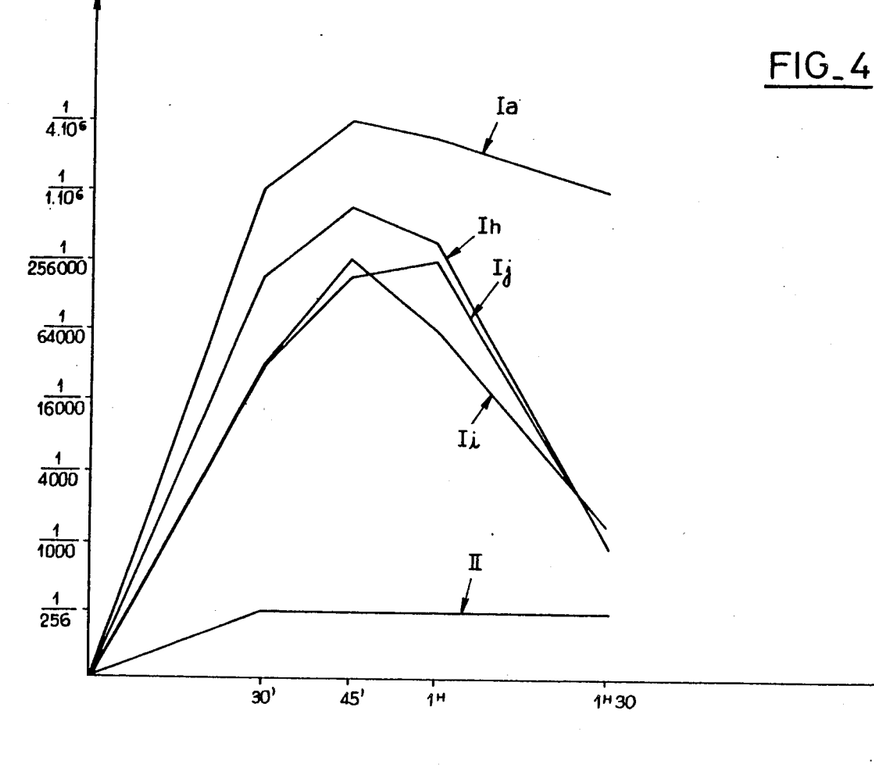

FIGS. 3 and 4 compare the activities obtained in vivo by the FTS passed over a chelating resin, then treated with different metals, that is the following metal salts:

| Zinc sulfate | (curve Id) |
|---|---|
| Copper sulfate | (curve Ie) |
| Ferrous sulfate | (curve If) |
| Cobalt chloride | (curve Ig) |

*-continued*

| Nickel chloride | (curve Ih) |
|---|---|
| Chromium chloride | (curve Ii) |
| Manganese chloride | (curve Ij) |
| Aluminum nitrate | (curve Ik) | and injected into the mouse, with the activity obtained using the FTS which was merely passed over a chelating resin and injected into the mouse (curve II).

Figure 5:
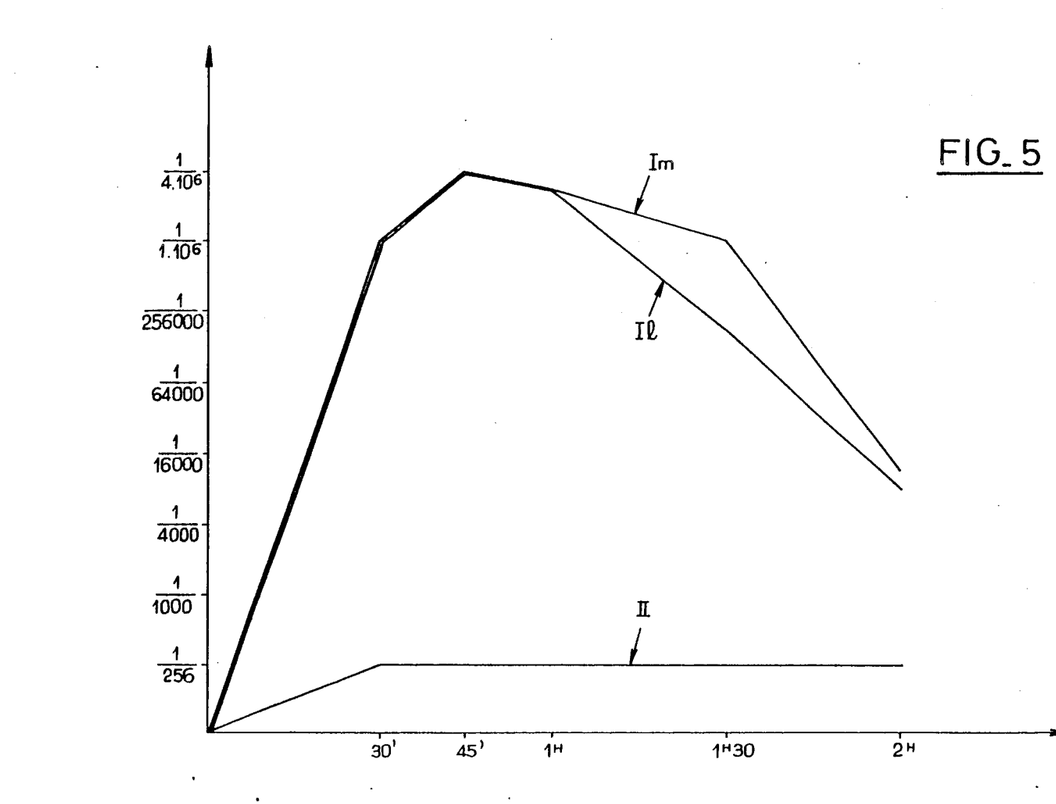

FIG. 5 shows the activity obtained in vivo by FTS passed over a chelating resin, then treated with zinc sulfate either for ten minutes at 20° C. (curve Il) or ten minutes at 37° C. (curve Im), and injected into the mouse, in comparison with the FTS which was merely passed over a chelating resin and injected into the mouse. This Figure shows that there are no significant differences in activation between the treatment effected at 20° C. and that effected at 37° C.

Figure 6:
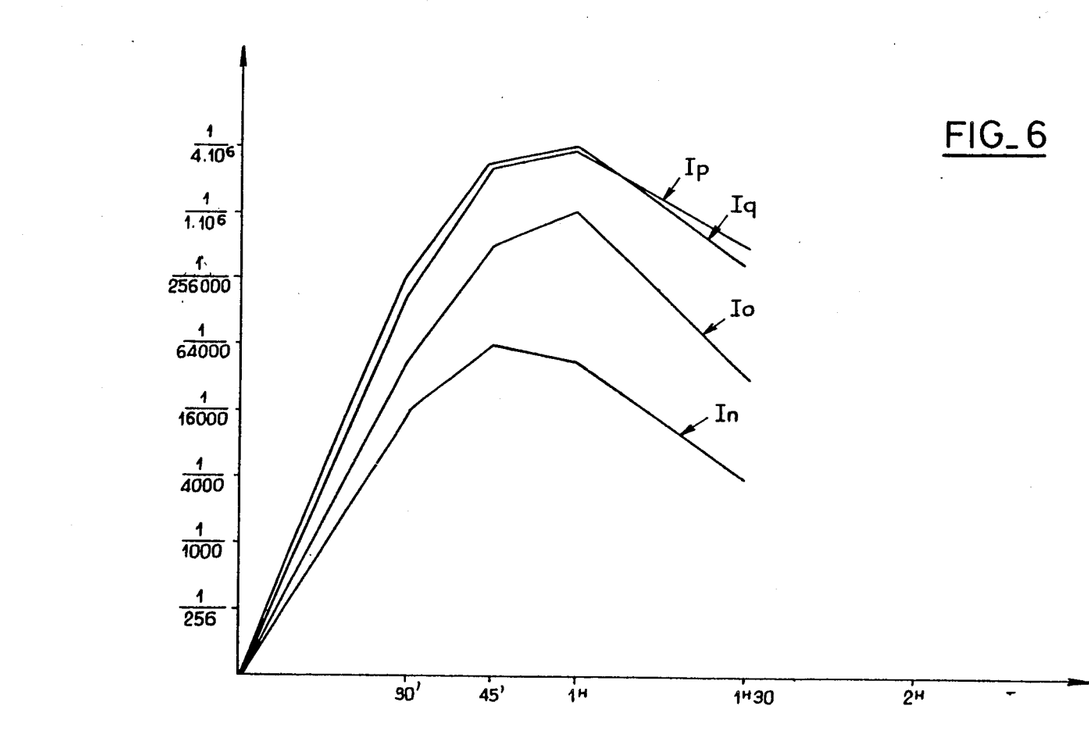

FIG. 6 shows the activity obtained in vivo by the FTS, which was passed over a chelating resin then treated with zinc compound, for different injection doses into the mouse: 0.001 ng(curve In), 0.01 ng(curve Io), 0.1 ng(curve Ip) and 1 ng(curve Iq).

At the same time, the in vivo treatment of thymectomised mice with the products of the invention completely restores the sensitivity to azathioprine and to the antitheta serum of the rosette-forming cells from the spleen of these mice, as is shown by the results in the Table II below:

TABLE II

Sensitivity of the spleen of thymectomised mice (Tx) to azathioprine, the mice being injected 24 hours before the test with 0.1 or 1 ng of reference FTS or of products of the invention.

| Treatment | Sensitivity of spleen to azathioprine |
|---|---|
| Untreated normal spleen | 0.7 Y |
| Untreated Tx spleen | 25 Y |
| Tx spleen treated with 1 ng of FTS passed over Chelex 100 | 25 Y |
| Tx spleen treated with 1 ng of reference | 0.7 Y |
| Tx spleen treated with 0.1 ng of FTS passed over Chelex 100 and treated with 0.1 ng of ZnSO₄ | 0.7 Y |
| Tx spleen treated with 0.01 ng of FTS passed over Chelex 100 and treated with 0.1 ng of ZnSO₄ | 0.7 Y |
| Tx spleen treated with 0.01 ng of FTS passed over Chelex 100 + activating fraction | 0.7 Y |
| Tx spleen treated with 0.01 ng of FTS passed over Chelex 100 + activating fraction passed over Chelex 100 | 25 Y |

These experiments were repeated using different doses of the products: from 1 to 100 pg, which allowed a demonstration of the relationship between the dose and effect and showed the absence of acute toxicity, whether the product is injected alone (in physiological serum) or absorbed on carboxymethyl cellulose.

These results show that in vivo a considerable activation is obtained by the zinc and, to a lesser extent, by other metals.

The products of the invention have the same pharmacological properties and the same therapeutic applications as FTS or its analogs or derivatives.

It has already been pointed out in the publications cited earlier on relating to FTS analogs and derivatives that these compounds may have either the same thymic activity as FTS or an inhibiting or antagonistic effect on this thymic activity.

The compounds which are active in the rosette test all have the same thymic activity as FTS whereas certain compounds which are inactive in the rosette test have an inhibiting or antagonistic effect on the thymic activity.

In every case, these derivatives may be used as medicaments for treating illnesses attributable to an unbalance of T lymphocytes, particularly auto-immune illnesses corresponding to a collapse of the suppressor lymphocytes, viral illnesses corresponding to a reduction in the "helper" lymphocytes and tumoral illnesses caused by a deficit of "Killer" lymphocytes.

Table III below shows the effect of the treatment with zinc on the biological activity of certain FTS analogs and derivatives.

Gln-Ala-Lys-Ser-Gln-Gly-Gly-Ser-Asn (18)
PyroGlu-D-Ala-Lys-Ser-Gln-Gly-Gly-Ser-Asn (47)
D-Ala-Lys-Ser-Gln-Gly-Gly-Scr-Asn (45)
PyroGlu-Ala-Lys-Ser-Gln-Gly-Gly-Ser-Asp (53)
PyroGlu-Ala-Lys-Ser-Gln-Gly-Gly-Ala-Asn (59)
PyroGlu-Ala-Lys-Ala-Gln-Gly-Gly-Ser-Asn (60)
Z Gln-Ala-Lys-Ser-Gln-Gly-Gly-Ser-Asn (34)
PyroGlu-Ala-D-Lys-Ser-Gln-Gly-Gly-Ser-Asn (61)
PyroGlu-Ala-Lys($N^6$-acetyl)-Ser-Gln-Gly-Gly-Ser-Asn (62)
PyroGlu-Ala-Orn-Ser-Gln-Gly-Gly-Ser-Asn (63)
PyroGlu-Ala-Lys-(N-methyl)Ser-Gln-Gly-Ser-Asn (64)
PyroGlu-Ala-Lys-D-Ser-Gln-Gly-Gly-Ser-Asn (66)
PyroGlu-Ala-Lys-Ser-D-Gln-Gly-Gly-Ser-Asn (71)
PyroGlu-Ala-(2,6-diaminohexynoyl)-Ser-Gln-Gly-Gly-Ser-Asn (77)
PyroGlu-Ala-Lys-Ser-Gln-Gly-Gly-Ser-Gln (79)

TABLE III

| Peptide | Biological activity (rosette test) | | Skin grafts | Activity in the presence of zinc | | Inhibitor | Combination with the antibodies | Receiver |
|---|---|---|---|---|---|---|---|---|
| | In vitro | In vivo | | In vitro | In vivo | | | |
| 36 | − | − | − | − | − | − | − | − |
| 37 | − | − | ND | | + | − | + | − |
| 38 | ± | ± | ND | | + | − | + | ± |
| 42 | − | − | ND | | | + | − | + |
| 18 | + | + | ND | | | − | + | + |
| 47 | − | − | ND | | ++ | − | + | − |
| 45 | − | − | ND | + | ++ | − | + | − |
| 53 | − | − | ND | − | − | + | − | + |
| 59 | − | − | ND | − | − | + | + | + |
| 60 | − | − | ND | + | + | − | ± | ± |
| 34 | + | + | ND | | | | + | + |
| 61 | + | + | KD | | | − | ± | + |
| 62 | + | +R | +R | | | | + | − |
| 63 | − | − | ND | | + | − | + | + |
| 64 | + | + | ND | | | | + | + |
| 66 | − | − | − | − | − | − | − | − |
| 71 | − | − | ND | − | − | | − | − |
| 77 | − | − | ND | − | − | − | + | ± |
| 79 | − | − | ND | − | − | + | − | + |
| 82 | − | − | ND | − | − | − | + | − |
| 83 | − | − | ND | − | − | − | + | − |
| 84 | − | − | NK | + | ++ | − | + | − |
| 85 | − | − | ND | − | − | − | + | − |
| 86 | − | − | ND | − | − | + | + | + |
| 88 | − | − | ND | − | − | − | ± | − |
| 89 | + | +R | R | − | ++ | − | + | + |
| 90 | + | +R | R | − | − | − | − | + |
| 91 | ± | ±R | ND | − | − | − | + | + |
| 93 | − | − | ND | − | − | + | − | + |
| 96 | − | − | ND | + | + | + | − | + |
| 97 | − | − | ND | − | − | + | − | + |
| 105 | + | + | ND | − | − | − | + | + |
| 106 | + | + | ND | − | − | − | + | + |
| 107 | + | + | ND | − | − | − | + | + |
| 109 | + | + | ND | − | − | − | + | + |
| 111 | − | − | ND | − | − | − | + | − |
| 112 | + | ++R | +́+R | − | − | − | + | + |
| 113 | − | − | | | | − | − | − |

It is important to note that certain peptides (Nos. 37, 38, 47, 45, 60, 63, 84 and 96) which are completely or substantially inactive in the rosette test become active after treatment with zinc.

In Table III, the letters ND stand for non-determined whilst the letter R means that the compound corresponds to a delayed activity, i.e. to a prolonged activity.

On the other hand, the peptide numbers correspond to the following peptides:
Ser-Gln-Gly-Gly-Ser-Asn (36)
Lys-Ser-Gln-Gly-Gly-Ser-Asn (37)
Ala-Lys-Ser-Gln-Gly-Gly-Ser-Asn (38)
PyroGlu-Ala-Lys-Ser-Gln-Gly-Gly-Ser (42)

Lys($N^6$acetyl)-Ser-Gln-Gly-Gly-Ser-Asn (82)
D-Lys-Ser-Gln-Gly-Gly-Ser-Asn (83)
Orn-Ser-Gln-Gly-Gly-Ser-Asn (84)
Na Z Lys-Ser-Gln-Gly-Gly-Ser-Asn (85)
PyroGlu-Ala-Lys-Ser-Glu-Gly-Gly-Ser-Ala-NH$_2$ (86)
Lys-Ser-Gln-D-Ala-Gly-Ser-Asn (88)
PyroGlu-Ala-Lys-Ser-Gln-D-Ala-Gly-Ser-Asn (89)
PyroGlu-Ala-Lys-Ser-Gln-Gly-Gly-Ser-D-Asn (90)
PyroGlu-Ala-Hep-Ser-Gln-Gly-Gly-Ser-Asn (91)
PyroGlu-Ala-Lys-Ser-Gln-Gly-Gly-Ser-Asn-NH$_2$ (93)
PyroGlu-Ala-Lys-Ser-Asn-Gly-Gly-Ser-Asn (96)
PyroGlu-Ala-Lys-Ser-Nva-Gly-Gly-Ser-Asn (97)
Z-Ala-Lys-Ser-Gln-Gly-Ser-Asn (105)

D-PyroGlu-Ala-Lys-Ser-Gln-Gly-Gly-Ser-Asn (106)
D-Gln-Ala-Lys-Ser-Gln-Gly-Gly-Ser-Asn (107)
Pro-Ala-Lys-Ser-Gln-Gly-Gly-Ser-Asn (109)
PyroGlu-Ala-Arg-Ser-Gln-Gly-Gly-Ser-Asn (111)
PyroGlu-Ala-Har-Ser-Gln-Gly-Gly-Ser-Asn (112)
PyroGlu-Ala-Lys-($N^6$-acetyl)-Ser-Gln-D-Ala-Gly-Ser-Asn (113)

In the above peptides, the aminoacids are designated by their standard abbreviations. In addition, the FIG. 2 denotes the benzyl oxycarbonyl group.

As mentioned above, the activated products according to the invention may be used in the treatment of illnesses attributable to an unbalance of T lymphocytes, particularly corresponding to:

a collapse of the suppressor lymphocytes: auto-immune illnesses, such as lupus, particularly lupus erythematosus, disseminated sclerosis, rhumatoid polyarthritis;

a reduction in the "helper" lymphocytes: bacterial and viral infections, particuarly herpes recurrens zona, varicella;

a deficit of "killer" lymphocytes: tumoral illnesses, in particular nasopharyngeal cancers, epidermoid cancer of the lung infiltrating cancer of the bladder, melanomas, neoplasms.

The products according to the present invention may be administered intravenuously or intramuscularly, in the form of suppositories, aerosols or orally in protected form. Suitable vehicles which may be used in the composition include for example sterile liquids, such as water, or a physiological solution or substances capable of imparting a delayed effect or even preparations capable of being administered in the form of suppositories, aerosols or sublingually. In addition to a vehicle, the compositions according to the invention may also comprise other ingredients, such as stabilisers, oxidation inhibitors, suspending agents or preservatives, such as phenol or chlorobutanol and agents of the same type. The final solution may readily be sterilised by conventional filtration techniques.

The composition used in accordance with the invention contains in aqueous solution a sufficient quantity of the agent according to the invention to be therapeutically effective. The doses to be administered depend to a large extent upon the condition and weight of the patient to be treated.

For example, it is possible to administer a dose of 100 to 5000 μg per injection and preferably 500 μg per injection repeated three times per week. This corresponds to an approximate dose of 10 γ/kg in humans.

The activated products according to the invention may also be used in the prepration of radioactive tracers suitable for use in radio-immunological detection processes for detecting the level of FTS present in the serum.

The rosette test has shown that the level of FTS in the serum is modified in certain immuno-pathological situations, such as lupus and myasthenic conditions (J. F. Bach et coll., Ann. N.Y. Acad. Sci. 249 (1975), page 186).

However, since the rosette test is a semi-quantitative test, there is a need to develop a quantitative detection process which is sufficiently sensitive to allow the direct detection of FTS in the blood.

The process according to the invention for detecting FTS in a sample is characterised in that a predetermined quantity of said sample is contacted with a predetermined quantity of tracer and with a predetermined quantity of anti-FTS antibody so as to bring about a competitive reaction between the tracer and the FTS of the sample in their combination with the anti-FTS antibody, the quantity of free tracer or tracer combined with the antibody is determined after the reaction has reached a state of equilibrium and the value obtained is compared with the values obtained for known and increasing quantities of FTS.

The anti-FTS antibody is prepared by fixing the FTS or one of its analogs or derivatives to a support to obtain an immunogen, injecting the immunogen into an animal and subsequently collecting the serum of the animal.

The tracer is obtained by labelling with a radioactive isotope and preferably by introducing an iodisable molecule into the activated product according to the invention and subsequently iodising the iodisable derivative thus obtained.

To carry out the detection process, it is possible to use a box of reactants optionally containing the tracer and the antibody required for detection.

The detection process is illustrated by the following Example.

EXAMPLE 4

I. Materials and Methods

A. Reactants

The synthetic FTS was prepared by the method described above.

B. Radioactive tracer

A synthetic analog of FTS, for example P-aminobenzoyl-Glnl-FTS, prepared by E. Bricas (Universite de Paris Sud Orsay), is labelled with iodine 125 in the presence of chloramine T (the P-aminobenzoyl-Glnl-FTS is only one example amongst others of FTS analogs or derivatives which may be used for preparing the radioactive tracer). The FTS-$^{125}$I is separated from the free iodine by filtration over Sephadex G-25 gel eluted with 0.1 M ph 7.6 tris-HCl buffer. Aliquot fractions of FTS-$^{125}$I (approximately $5 \times 10^6$ cpm) are mixed with a suspension of chelex 100 (50 mg/ml), followed by incubation for 30 minutes in the presence of 100 ng of zinc chloride. The mixture is then chromatographed on Biogel P2, eluted with 0.1 M pH 7.6 tris-HCl buffer. The peak corresponding to the FTS-Zn is recovered and used for radio-immunological detection.

C. Anti-FTS antibody

The FTS is rendered immunogenic by fixing it to bovine albumin serum in the presence of glutaraldehyde (6). The immunogen thus obtained, incorporated in Freund's complete adjuvant, is injected into rabbits (1 mg per rabbit). A booster injection (also of 1 mg) is administered 1 month after the first injection and the animals are bled 15 days after the booster injection.

D. Preparation of the biological samples

Fresh serums from normal and thymectomised mice are ultrafiltered on Amicon CF50 and used extemporaneously.

II. RESULTS

A. Comparison of the antigenicity of the two tracers

The antiserum obtained by immunisation against the synthetic FTS combines the two tracers under investigation and (FTS$^{125}$I and FTS--Zn$^{125}$I). Defined as the maximum dilution of the antiserum which produces a 40% combination of the radioactive tracer, the strength of the antiserum is 1/50 000 for FTS$^{125}$I and 1/20 000 for FTS-Zn$^{125}$I.

B. Displacement of the combination by FTS and by the serum of normal or thymectomised mice The synthetic FTS inhibits the combination of the two tracers with the antibody, the inhibition level reaching 80% at the highest concentrations of the peptide. The sensitivity of detection as expressed by the hormone dose which inhibits 50% of the combination is 10 pg for FTS$^{125}$I and 60–80 pg for FTS-Zn$^{125}$I.

Ten samples of serum from normal mice and ten samples of serum from thymectomised mice were compared for their ability to displace the combination of the two tracers described above with the rabbit antiserum. No significant difference is observed with FTS$^{125}$I between the serums emanating from normal and thymectomised animals. On the other hand, although the ten samples from normal mice all displace the combination of the FTS Zn$^{125}$I, none of the serums from the thymectomised mice (even when used in undiluted form) affects the combination. The displacement obtained with the normal serums (diluted to ½) varies from 40 to 60% according to the samples. The displacement is still significant when the serums are diluted to 1/8th.

III. DISCUSSION

The foregoing results show that the antibodies obtained in rabbits after immunisation against synthetic FTS combine both the FTS and the FTS-Zn tracers, albeit to a lesser extent in the case of FTS-Zn. The synthetic FTS displaces the combination of the two tracers with the antiserum. By contrast, under the conditions of these tests, the FTS of biological origin present in the serum of normal mice only inhibits the combination of the FTS-Zn tracer, the specificity of inhibition being demonstrated by the complete absence of displacement observed with the serum of thymectomised mice.

These results confirm the existence of two forms of FTS, one having picked up a metal, in the present case zinc, and having increased biological active and antigenically close to natural hormone and the other, free from metal, being antigenically different from thymic hormone.

It is still difficult to tell whether the rabbits immunised with synthetic FTS produced two families of antibodies each recognising one form of the peptide (with or without zinc) or instead only one antibody giving rise to a crossed reaction between the FTS and the FTS-Zn (but recognising the FTS with greater affinity than the FTS-Zn). This hypothesis is compatible with the significant (more than 50%) displacement of the combination of the FTS-Zn tracer observed both with synthetic FTS and with natural FTS. It implies that natural FTS only displaces the FTS-Zn tracer to which it is structurally closer than the zinc-free FTS and has no effect on the combination of the zinc-free FTS tracer for which the rabbit antibody has a greater affinity.

EXAMPLE 5

The following example illustrates the activity of the compositions according to the invention in the treatment of rheumatoid arthritis.

The tests were carried out on two groups of patients suffering from rheumatoid arthritis.

The pharmaceutical compositions used are the following:

| Lyophilized bottle | 1 mg | 100 µg |
|---|---|---|
| STF | 1 mg | 100 µg |
| Zinc chloride | 166 µg | 16.4 µg |
| Lactose | 10 mg | 10 mg |
| Water for injectable preparation q.s.p. | 1 ml | 1 ml |
| Solvent | | |
| Sodium chloride | 3.418 mg | 3.675 mg |
| Water for injectable preparation q.s.p. | 0.5 ml | 0.5 ml |

8 patients received subcutaneous injections of 150 ug, obtained from 2 100 µg bottles, each day for 15 days and then three times per week for 4 months. The other 8 patients received 1 mg of the composition by the same protocol.

The characteristics of the patients are shown in the following Table V:

TABLE V

| Patients | STF 150 µg n = 8 | STF 1 mg n = 8 |
|---|---|---|
| Sex (male/female) | 0/8 | 2/6 |
| Average age (years) (sd) | 55.2 (11.2) | 60.4 (6.5) |
| Average duration of RA (years) (sd) | 15.1 (4.9) | 16.5 (7.4) |
| Rheumatoid nodules | 5/8 | 7/8 |
| Sjögren's syndrome | 3/8 | 3/8 |
| Rheumatoid factor (positive) | 6/8 | 6/8 |
| SAAD* treatment: | | |
| gold salt | 5/8 | 6/8 |
| antimalarial compound | 1/8 | 3/8 |
| penicillamine | 6/8 | 4/8 |
| thiopronine | 4/8 | 5/8 |
| chlorambucil | 2/8 | 1/8 |
| Intake of prednisone (number of patients) | 7/8 | 5/8 |
| Intake of AINS** (number of patients) | 8/8 | 8/8 |

* SAAD = slow-action antirheumatic compound
** AINS = antiinflammatory non-steroid compound The patients have not been treated with slow-action antirheumatic compounds for at least 3 months before the start of the test.

In all cases, rheumatoid arthritis is developing in spite of the use of antiinflammatory agents.

The patients continued to use analgesics and/or antiinflammatory agents during the treatment.

The biological and clinical studies are carried out monthly by the same person.

The changes in the results are evaluated after 4 months of treatment.

The attached Table VI summarizes the clinical parameters observed at the start of treatment and 4 months thereafter:

TABLE VI

| Parameters | STF 150 µg (n = 8) | | FTS 1 mg (n = 8) | |
|---|---|---|---|---|
| | before the test | average change after 4 months | before the test | average change after 4 months |
| Morning stiffness (minutes) | 136 (107) | −42 (128) | 151 (128) | −52.5 (90.6) |
| Articular index (Ritchie) | 12.9 (5.7) | +0.63 (5.9) | 13.4 (4.6) | −5.4 (3.2)*** |
| Swollen joints (number) | 17.3 (6.8) | −1.38 (3.4) | 17.6 (8.5) | −5.0 (4.9)** |

TABLE VI-continued

| Parameters | STF 150 μg (n = 8) | | FTS 1 mg (n = 8) | |
| --- | --- | --- | --- | --- |
| | before the test | average change after 4 months | before the test | average change after 4 months |
| Gripping strength (mm Hg) | 257 (130) | +44.4 (63.4)* | 258 (195) | −6.8 (205) |
| IPP circumference (mm) | 593 (26.0) | −8.9 (11.4)* | 617 (56) | −9.6 (9.5)** |
| Pain (mm) | 71.8 (17.8) | −1.63 (19.9) | 54.9 (36.6) | −6.5 (23) |
| Functional index (Lee) | 12.1 (3.2) | +0.25 (1.8) | 13.4 (3.8) | −0.9 (1.8) |
| E.S.R. (mm/h) | 53.1 (14.5) | +3.1 (6.8) | 58.0 (27.2) | −7.5 (22.7) |

*p 0.10
**p 0.05
***p 0.01

In general, no unfavorable secondary effect at all is observed.

In the grou of patients who were treated with 150 ug compositions of FTS, the only changes observed in the various parameters are the improvement in the gripping strength and the reduction in the IPP circumference.

With compositions containing 1 mg of FTS, a significant improvement in the Ritchie index, which takes into account the various criteria connected with rheumatoid arthritis (gripping strength, morning stiffness and the like), a reduction in the number of swollen joints and a reduction in the IPP circumference are observed.

Taking into account these very satisfactory results and the absence of a secondary reaction, the compositions according to the present invention constitute a particularly useful therapy in the long-term treatment of these diseases, that is, rheumatoid polyarthritis.

We claim:

1. A process for the preparation of a new product from a starting material selected from the serum thymic factor and its analogs and derivatives, which comprises reacting said starting material with a reactant containing metal ions or a metal-containing protein substance, said metal being capable of forming a IV co-ordination complex having a tetrahedral phase.

2. A process according to claim 1 wherein the serum thymic factor is a polypeptide having the sequence X-Gln-Gly-Gly-Y wherein Y represents Ser-Asn or -Ser and X represents Ser-, Lys-Ser-, Ala-Lys-Ser-, Glx-Ala-Lys-Ser-, wherein Glx is Pyro-Glu- or Glu; and the derivatives thereof.

3. The process of claim 1 wherein said starting material is brought into contact with a metal or one of its salts for 10 to 30 minutes at a pH-value of from 7 to 9.

4. The process of claim 3 wherein said starting material is used in a proportion of 1 mole for 0.1 to 10 moles of metal or metal salt.

5. The process of claim 1 wherein said metal is selected from the group consisting of divalent and trivalent metals.

6. The process of claim 5, wherein the reactant is a zinc salt.

7. A process as claimed in claim 1 wherein the metal-containing protein substance is a serum fraction.

8. The process of claim 1, wherein the metal-containing protein substance is a fraction of a thymic extract.

9. The process of claim 8, wherein the metal-containing protein substance is a fraction of the Thymosine Fraction 5.

10. The process of claim 9, wherein said starting material is incubated with said fraction, the mixture obtained after incubation is fractionated and the fraction with the greatest activity in the rosette test is selected.

11. The process of claim 10, wherein said incubation is carried out for 10 minutes to 1 hour at a pH-value of from 6 to 8 and at a temperature of from 30° to 40° C.

12. The process of claim 1, wherein the starting material is reacted with a chelating agent capable of chelating metals and then reacted with said reactant.

13. A complex of serum thymic factor and its analogs and derivatives with a metal, or a metal-containing protein substance which is capable of forming a IV coordination complex having a tetrahedral configuration.

14. The complex of claim 13, wherein the metal is selected from divalent and trivalent metals.

15. The complex of claim 13 wherein the metal is aluminum or zinc.

16. The complex of claim 13 wherein the ratio by weight of metal to the complex is greater than 1:200.

17. The complex of claim 13 wherein the serum thymic factor is a polypeptide having the sequence X-Gln-Gly-Gly-Y wherein Y represents Ser-Asn or -Ser and X represents Ser-, Lys-Ser-, Ala-Lys-Ser-, Glx-Ala-Lys-Ser- wherein Glx is Pyro-Glu- or Glu-, and the derivatives thereof.

18. The complex of claim 13 wherein the metal-containing protein substance is a fraction of a thymic extract.

19. The complex of claim 18 wherein the protein substance is Thymosine Fraction 5.

20. A process for preparing a peptide containing composition suitable for use in the treatment of an unbalance of T lymphocytes in a host which comprises contacting a thymic extract or a serum thymic factor containing a nonapeptide of the sequence:

pGlu-Ala-Lys-Ser-Gln-Gly-Ser-Asn with a reactant selected from the group consisting of metal, metal salts and metal-containing protein substances, said metal being capable of forming a IV co-ordination complex having a tetrahedral shape.

21. The process of claim 44 wherein the reactant is a zinc salt.

22. A complex of a metal capable of forming a IV co-ordination complex having a tetrahedral shape and a peptide selected from the group consisting of
Gln-Ala-Lys-Ser-Gln-Gly-Gly-Ser-Asn
PyroGlu-D-Ala-Lys-Ser-Gln-Gly-Gly-Ser-Asn
PyroGlu-Ala-Lys-Ser-Gln-Gly-Gly-Ser-Asp
PyroGlu-Ala-Lys-Ser-Gln-Gly-Gly-Ala-Asn
PyroGlu-Ala-Lys-Ala-Gln-Gly-Gly-Ser-Asn
Z Gln-Ala-Lys-Ser-Gln-Gly-Gly-Ser-Asn PyroGlu-Ala-D-Lys-Ser-Gln-Gly-Gly-Ser-Asn
PyroGlu-Ala-Lys(n⁶-Acetyl)-Ser-Gln-Gly-Gly-Ser-Asn
PyroGlu-Ala-Orn-Ser-Gln-Gly-Gly-Ser-Asn
PryoGlu-Ala-Lys-D-Ser-Gln-Gly-Gly-Ser-Asn
PyroGlu-Ala-Lys-Ser-D-Gln-Gly-Gly-Ser-Asn
PyroGlu-Ala-lys-Ser-Gln-Gly-Gly-Ser-Gln
PyroGlu-Ala-Lys-Ser-Gln-Gly-Gly-Ser-B-Ala-NH₂
PyroGlu-Ala-Lys-Ser-Gln-D-Ala(Gly-ser-Asn)
PyroGlu-Ala-Lys-Ser-Gln-Gly-Gly-Ser-D-Asn
PyroGlu-Ala-Lys-Ser-Gln-Gly-Gly-Ser-Asn-NH₂
PyroGlu-Ala-Lys-Ser-Asn-Gly-Gly-Ser-Asn
PyroGlu-Ala-Lys-Ser-Nva-Gly-Gly-Ser-Asn
D-PyroGlu-Ala-Lys-Ser-Gln-Gly-Gly-Ser-Asn
D-Gln-Ala-Lys-Ser-Gln-Gly-Gly-Ser-Asn
Pro-Ala-Lys-Ser-Gln-Gly-Gly-Ser-Asn
PyroGlu-Ala-Arg-Ser-Gln-Gly-Gly-Ser-Asn
PyroGlu-Ala-Har-Ser-Gln-Gly-Gly-Ser-Asn and
PyroGlu-Ala-Lys-(N⁶-acetyl)-Ser-Gln-D-Ala-Gly-Ser-Asn.

23. A complex of a metal capable of forming a IV co-ordination complex having a tetrahedral shape and a peptide selected from the group consisting of
Ala-Lys-Ser-Gln-Gly-Gly-Ser-Asn
PyroGlu-Ala-Lys-Ser-Gln-Gly-Gly-Ser
D-Ala-Lys-Ser-Gln-Gly-Gly-Ser-Asn
PyroGlu-Ala-Lys-(N-methyl)Ser-Gln-Gly-Ser-Asn
PyroGlu-Ala-(2, 6-diaminohexynol)-Ser-Gly-gly-gly-Ser-Asn and
PyroGlu-Ala-Hep-Ser-Gln-Gly-gly O Ser-Asn.

24. a complex of a metal capable of forming a IV co-ordination complex having a tetrahedral shape and a peptide selected from the group consisting of
Lys(N⁶acetyl)-Ser-Gln-Gly-Ser-Asn
D-Lys-Ser-Gln-Gly-Gly-Ser-Asn
Orn-Ser-Gon-Gly-Gly-Ser-Asn
Na Z.Lys-Ser-Gln-gly-Gly-Ser-Asn
Lys-Ser-Gln-D-Ala-Gly-Ser-Asn
Z-Ala-Lys-Ser-Gln-Gly-Ser-Asn and
Lys-Ser-Gln-Gly-Gly-Ser-Asn.

25. A complex of a metal capable of forming a IV co-ordination complex having a tetrahedral shape and a peptide having the amino acid sequence Ser-Gln-Gly-Gly-Ser-Asn.

26. A tracer comprising the complex of claim 22 labelled by a radioactive isotope.

27. A tracer as claimed in claim 26, wherein an iodisable molecule is introduced into the complex and the iodisable derivative thus obtained is subsequent iodised.

28. A process for detecting serum thymic factor contained in a sample, wherein said sample is contacted with the tracer of claim 26 and anti-serum thymic factor antibody so as to bring about a competitive reaction between the tracer and the serum thymic factor of the sample in their combination with the anti-serum thymic factor antibody, the quantity of free tracer or tracer combined with the antibody is determined after the reaction has reached a state of equilibrium, and the value obtained is compared with the values obtained from known and increasing quantities of serum thymic factor.

29. A polypeptide having the sequence X-Gln-Gly-Gly-Y wherein Y is -Ser-Asn and X is Lys-Ser, Ala-Lys-Ser or Glx-Ala-Lys-Ser- wherein Glx is PyroGlu or Gln; and when X is Glx-Ala-Lys-Ser, Y can also be -Ser; and said polypeptide in which one or two amino acids in said sequence are replaced as follows:

a. Ser⁴ or Ser⁸ is replaced by: Thr, Ala or N-methyl-Ser;

PyroGlu is replaced by Pro;

c. Lys³ is replaced by: (N⁶-acetyl)-Lys, 2-aminohexanoyl, 2-6-diaminohexynoyl, Arg, Har or Orn.;

d. Gln⁵ is replaced by: Glu, Met(0), Asn or Nor-Val;

e. Gly⁶ or Gly⁷ either one individually, is replaced by: Ala, Sar or Leu, and Asn-NH₂, and the polypeptides, PyroGlu-Ala-Lys-Ser-Gln-Gly-Gly-Gly-Ser-Asn, and PyroGlu-Ala-Lys-Ser-Gln-Gly-Ser-Asn, with the proviso that the unmodified polypeptides PyroGlu-Ala-Lys-Ser-Gln-Gly-Gly-Ser-Asn and Gln-Ala-Lys-Ser-Gln-Gly-Gly-Ser-Asn are not included.

30. The polypeptide of claim 29 wherein an L-amino acid or modified amino acid of the general formula has been replaced by the corresponding amino acid of the D-configuration.

31. A polypeptide according to claim 29 which is PyroGlu-D-Ala-Lys-Ser-Gln-Gly-Gly-Ser-Asn.

32. A polypeptide according to claim 29 which is D-Ala-Lys-Ser-Gln-Gly-Gly-Ser-Asn.

33. A polypeptide according to claim 29 which is PyroGlu-Ala-Lys-Ala-Gln-Gly-Gly-Ser Asn.

34. A polypeptide according to claim 29 which is PyroGlu-Ala-Orn-Ser-Gln-Gly-Gly-Ser-Asn.

35. A polypeptide according to claim 29 which is PyroGlu-Ala-Lys-Ser Glu-Gly-Gly-Ser-Asn.

36. A polypeptide according to claim 29 which is Orn-Ser-Gln-Gly-Gly-Ser-Asn.

37. A polypeptide according to claim 29 which is PyroGlu-Ala-Hep-Ser-Gln-Gly-Gly-Ser-Asn.

38. A polypeptide according to claim 29 which is PyroGlu-Ala-Lys-Ser-Gln-Gly-Gly-Ser-Asn-NH₂.

39. A polypeptide according to claim 29 which is PyroGlu-Ala-Lys-Ser-Asn-Gly-Gly-Ser-Asn.

40. A polypeptide according to claim 29 which is PyroGlu-Ala-Lys-Ser-Nva-Gly-Gly-Ser-Asn.

41. A polypeptide according to claim 29 which is Z-Ala-Lys-Ser-Gln-Gly-Gly-Ser-Asn.

42. A polypeptide according to claim 29 which is D-PyroGlu-Ala-Lys-Ser-Gln-Gly-Gly-Ser-Asn.

43. A polypeptide according to claim 29 which is D-Gln-Ala-Lys-Ser-Gln-Gly-Gly-Ser-Asn.

44. A polypeptide according to claim 29 which is Pro-Ala-Lys-Ser-Gln-Gly-Gly-Ser-Asn.

45. A polypeptide according to claim 29 which is PyroGlu-Ala-Har-Ser-Gln-Gly-Gly-Ser-Asn.

46. The pharmaceutical composition effective for the treatment of rheumatoid arthritis which composition comprises a biologically acceptable carrier and an effective amount for the treatment of rheumatoid arthritis of the complex of any one of claims 13, 14, 15 or 16.

47. The pharmaceutical composition effective for the treatment of illness attributed to an unbalance of T lymphocytes which comprises a biologically acceptable carrier and an effective amount to treat an illness attributable to an unbalance of T lymphocytes of the complex of any one of claims 13, 14, 15 or 16.

* * * * *